United States Patent
Cannon et al.

(10) Patent No.: US 8,673,912 B2
(45) Date of Patent: Mar. 18, 2014

(54) CRYSTALLINE FORMS ON N-[3-FLUORO-4-({6-(METHYLOXY)-7-[(3-MORPHOLIN-4-YLPROPYL)OXY]-QUINOLIN-4-YL}OXY)PHENYL]-N'-(4-FLUOROPHENYL)CYCLOPROPANE-1,1-DICARBOXAMIDE

(75) Inventors: Hilary Cannon, Hitchin (GB); David Igo, Durham, NC (US); Tri Tran, Sacramento, CA (US)

(73) Assignee: Exelixis, Inc., South San Francisco, CA (US)

( * ) Notice: Subject to any disclaimer, the term of this patent is extended or adjusted under 35 U.S.C. 154(b) by 46 days.

(21) Appl. No.: 13/384,451

(22) PCT Filed: Jul. 16, 2010

(86) PCT No.: PCT/US2010/042353
§ 371 (c)(1),
(2), (4) Date: Jul. 12, 2012

(87) PCT Pub. No.: WO2011/009095
PCT Pub. Date: Jan. 20, 2011

(65) Prior Publication Data
US 2012/0270872 A1    Oct. 25, 2012

Related U.S. Application Data

(60) Provisional application No. 61/226,509, filed on Jul. 17, 2009.

(51) Int. Cl.
*A61K 31/535* (2006.01)
*C07D 413/12* (2006.01)

(52) U.S. Cl.
USPC ........................................ 514/237.2; 544/128

(58) Field of Classification Search
USPC ........................................ 514/237.2; 544/128
See application file for complete search history.

(56) References Cited

FOREIGN PATENT DOCUMENTS

WO    2005/030140    4/2005

OTHER PUBLICATIONS

International Search Report mailed Oct. 27, 2010 for PCT/US2010/042353.

*Primary Examiner* — Rebecca Anderson
(74) *Attorney, Agent, or Firm* — Honigman Miller Schwartz and Cohn LLP; Heidi M. Berven; Jonathan P. O'Brien

(57) ABSTRACT

This invention relates to three crystalline forms of N-[3-fluoro-4-((6-(methyloxy)-7-[(3-morpholin-4-ylpropyl)oxy]quinolin-4-ylloxy)phenyl]-N'-(4-fluorophenyl)cyclopropane-1,1-dicarboxamide. Compound (I), designated as Form A, Form B, and Form C. The invention provides methods for treatment of cancer by exploiting the modulation of protein kinase activity. The invention also provides pharmaceutical compositions containing a crystalline form of Compound (I) and a pharmaceutically acceptable excipient.

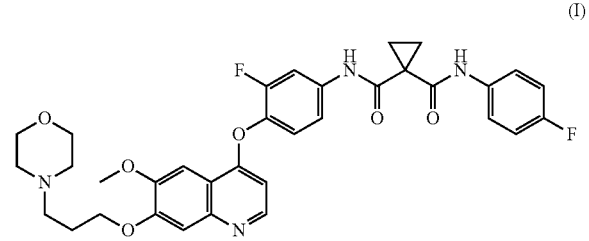

(I)

10 Claims, 18 Drawing Sheets

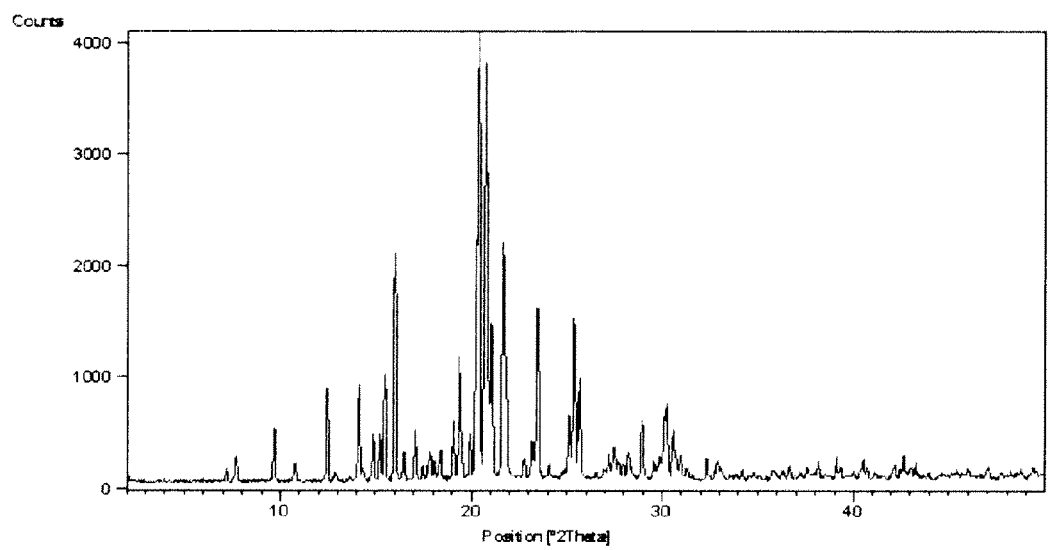
Fig. 1-A.

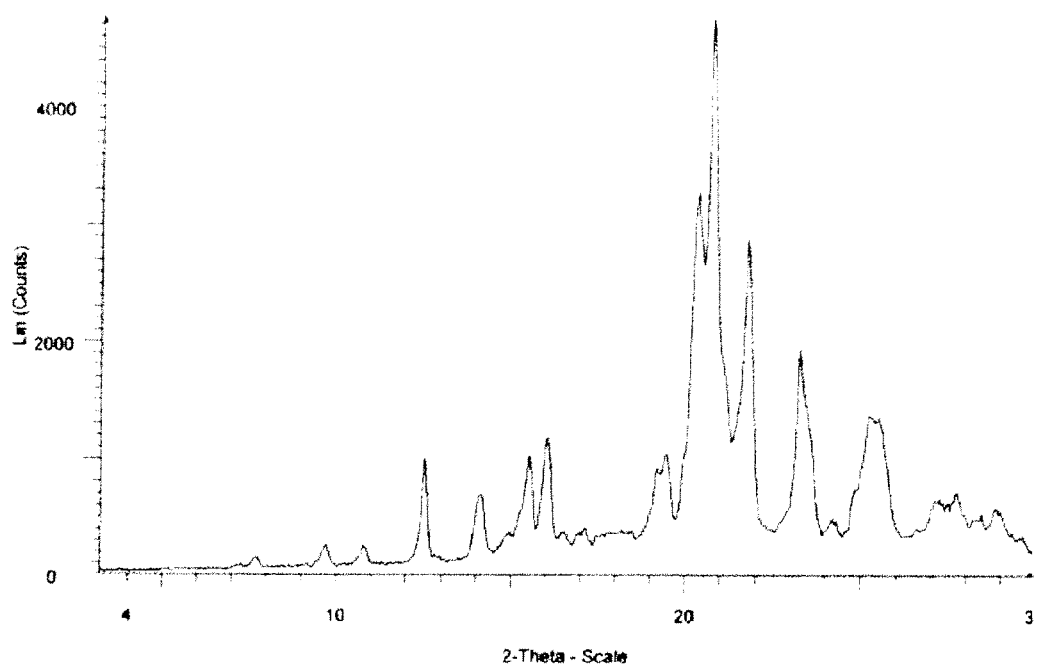
Fig. 1-B.

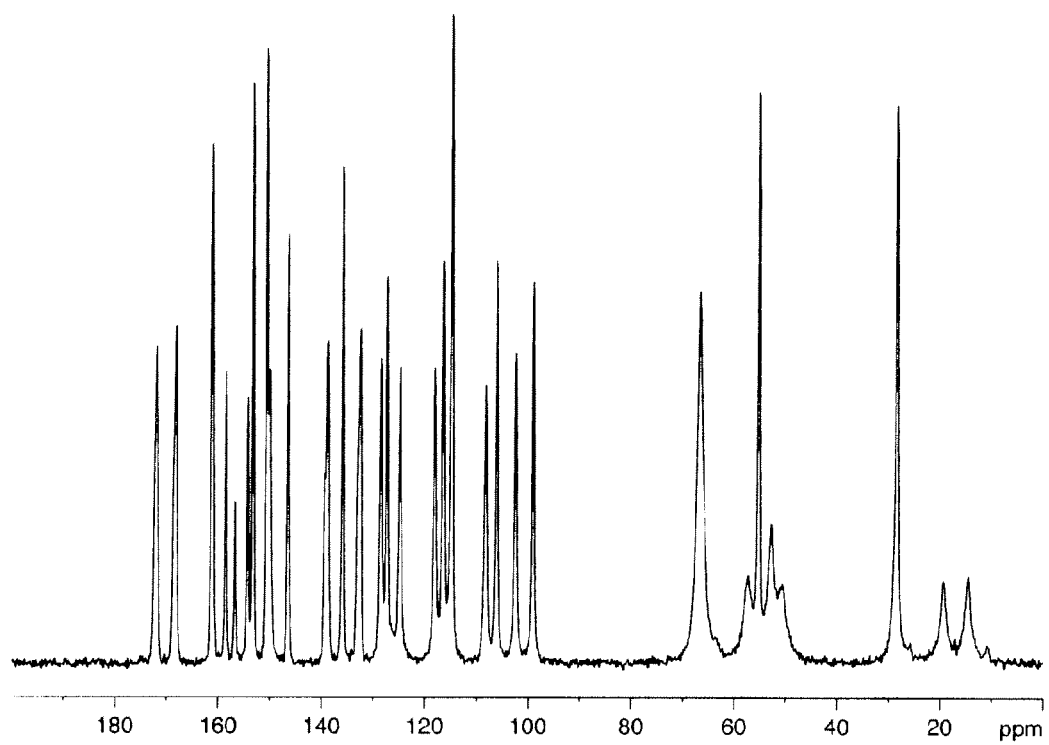
Fig. 1-C.

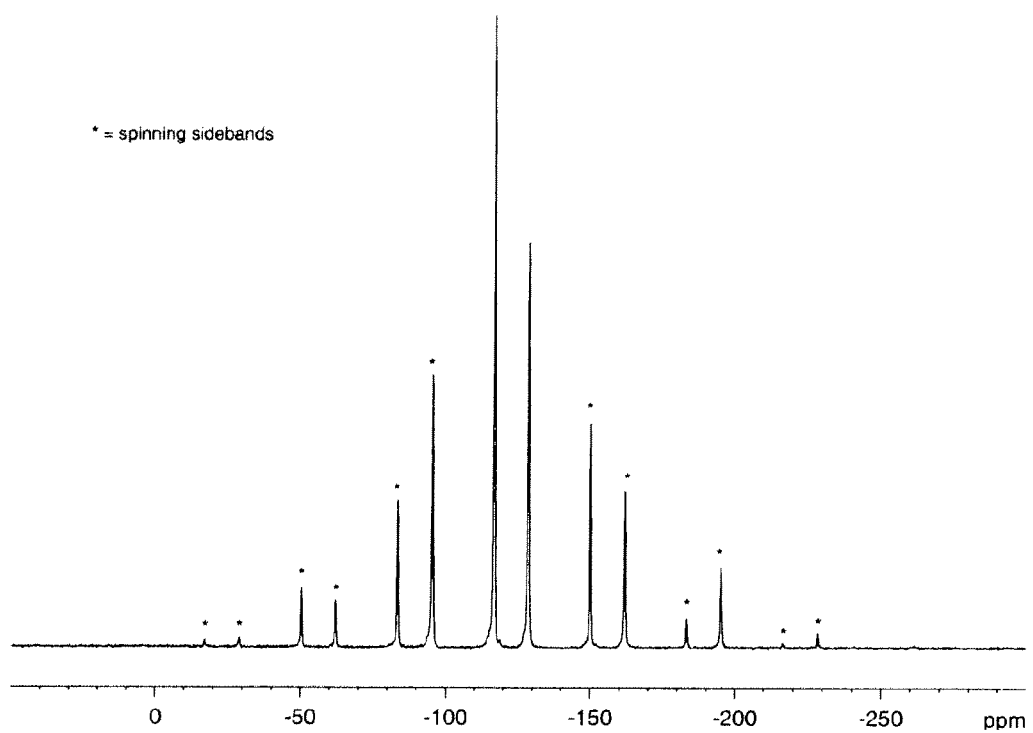
Fig. 1-D.

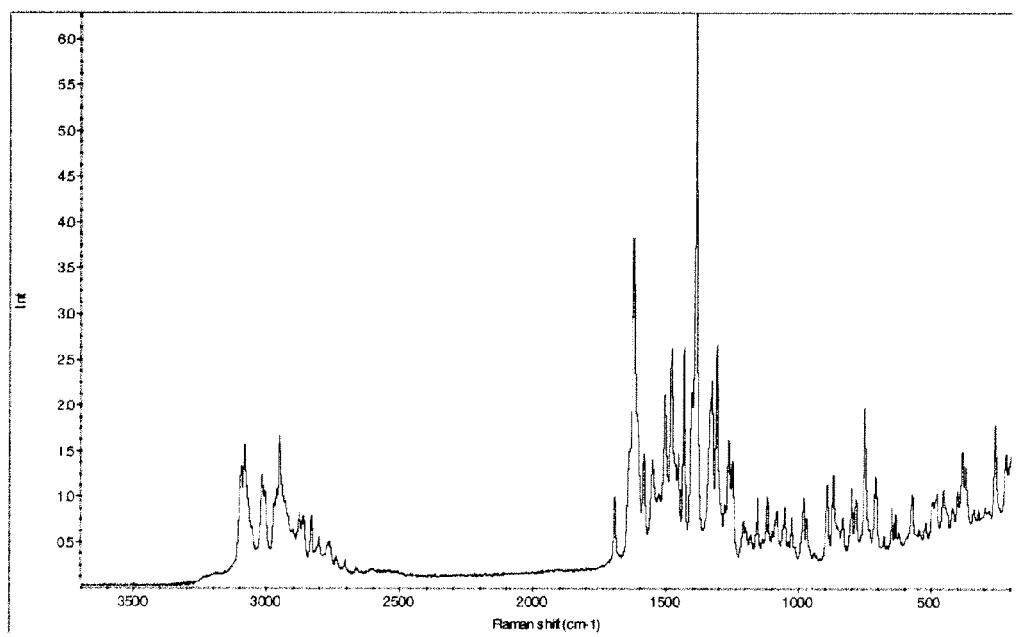
Fig. 1-E.

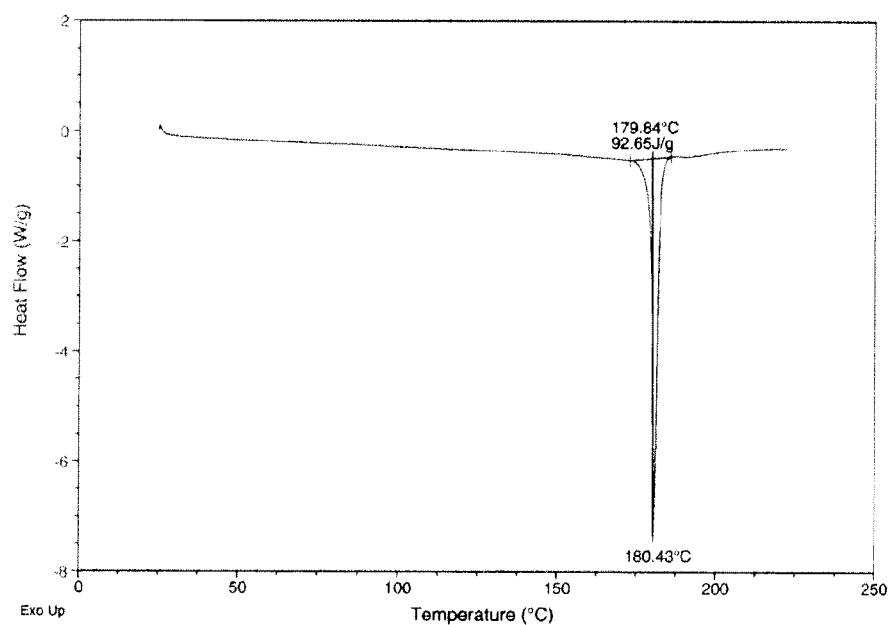
Fig. 1-F.

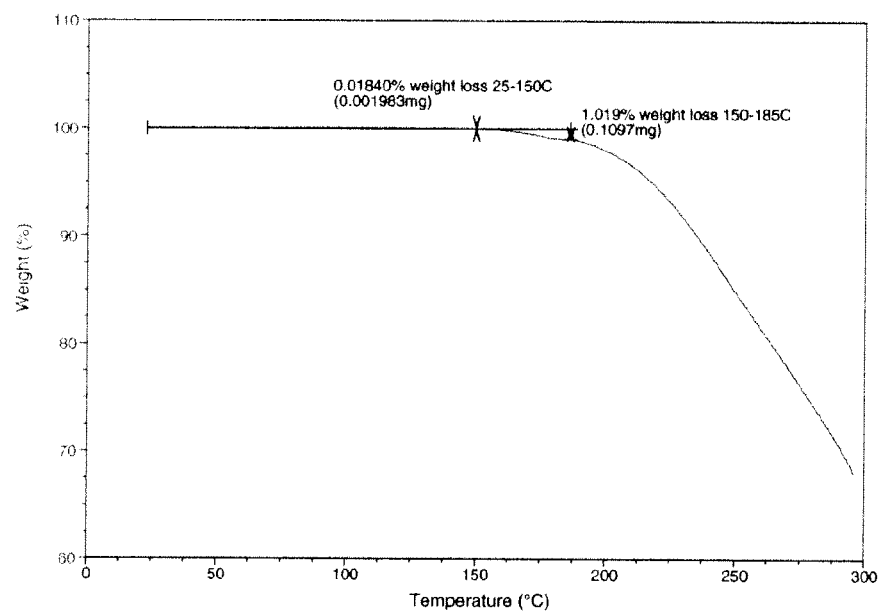
Fig. 1-G.

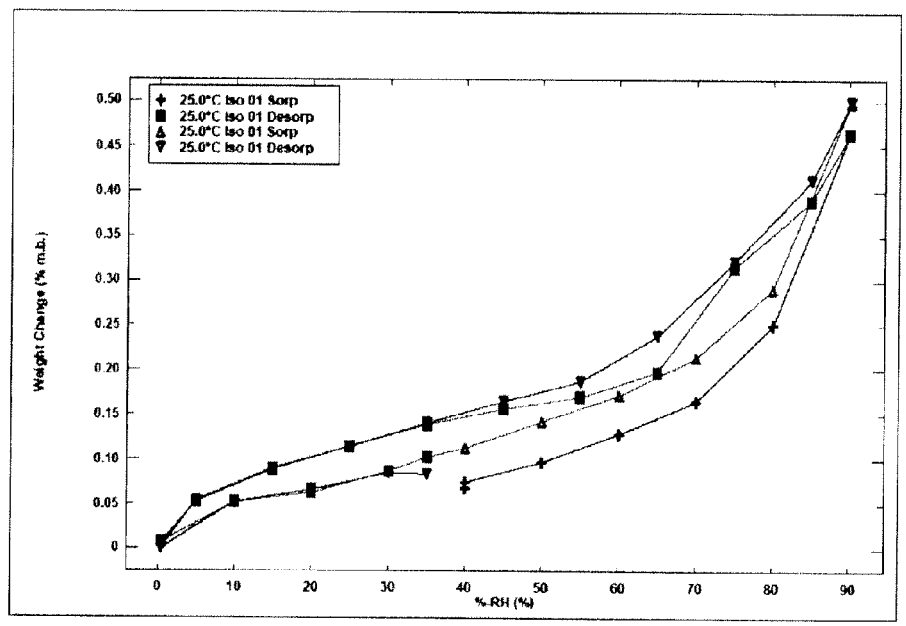
Fig. 1-H.

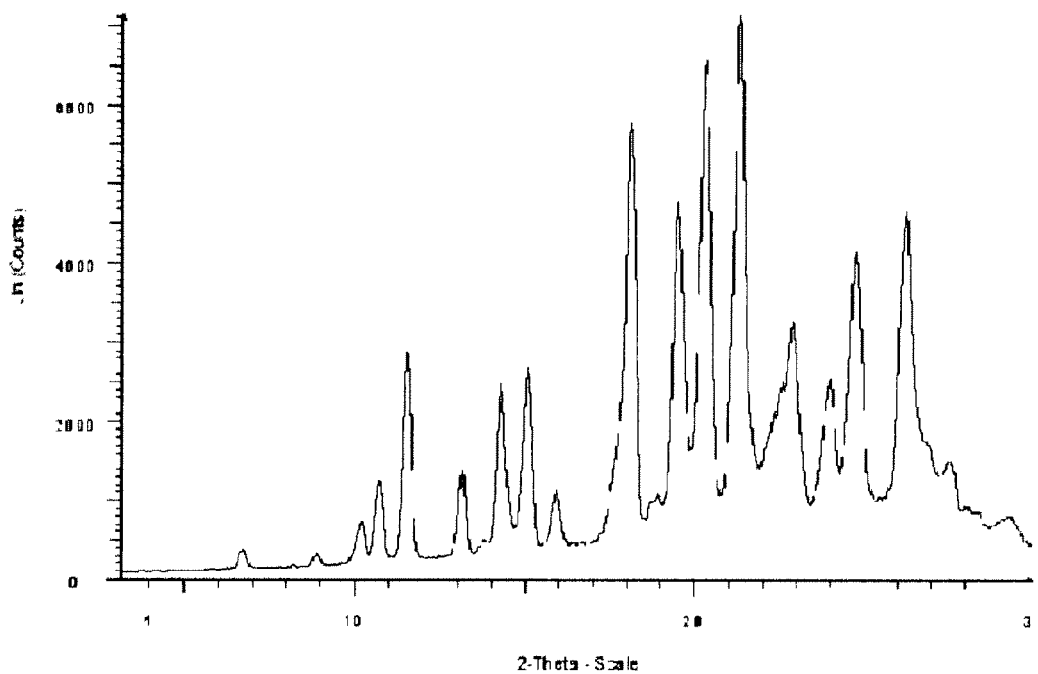
Fig. 2.1-A.

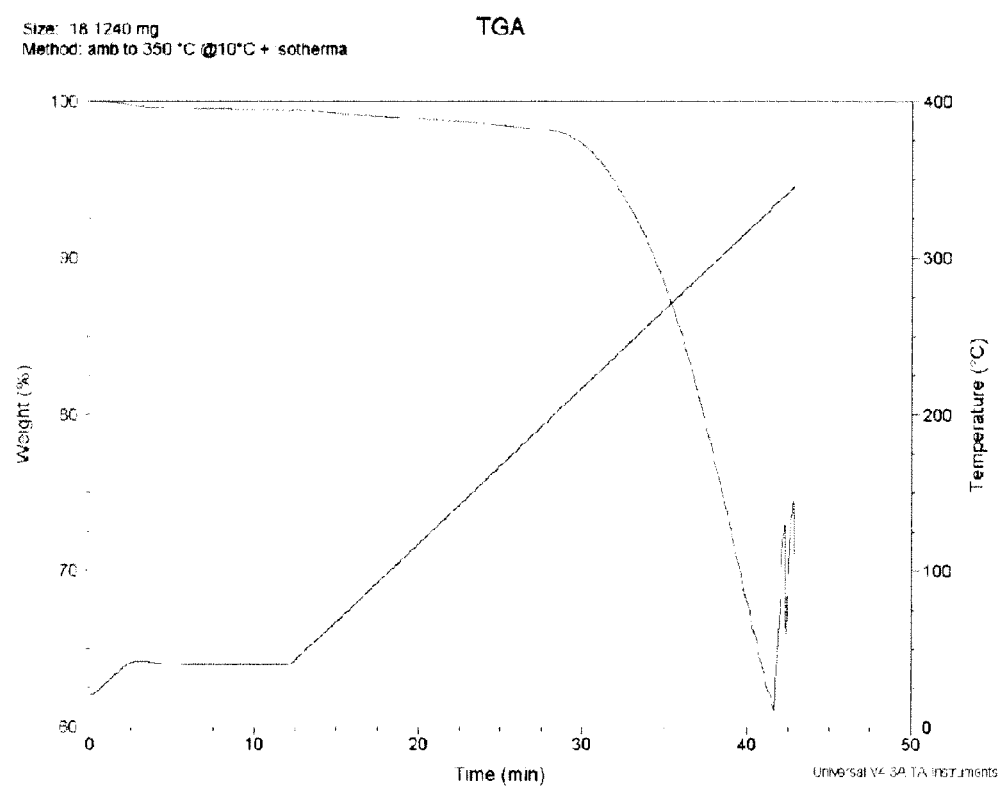
Fig. 2.1-B.

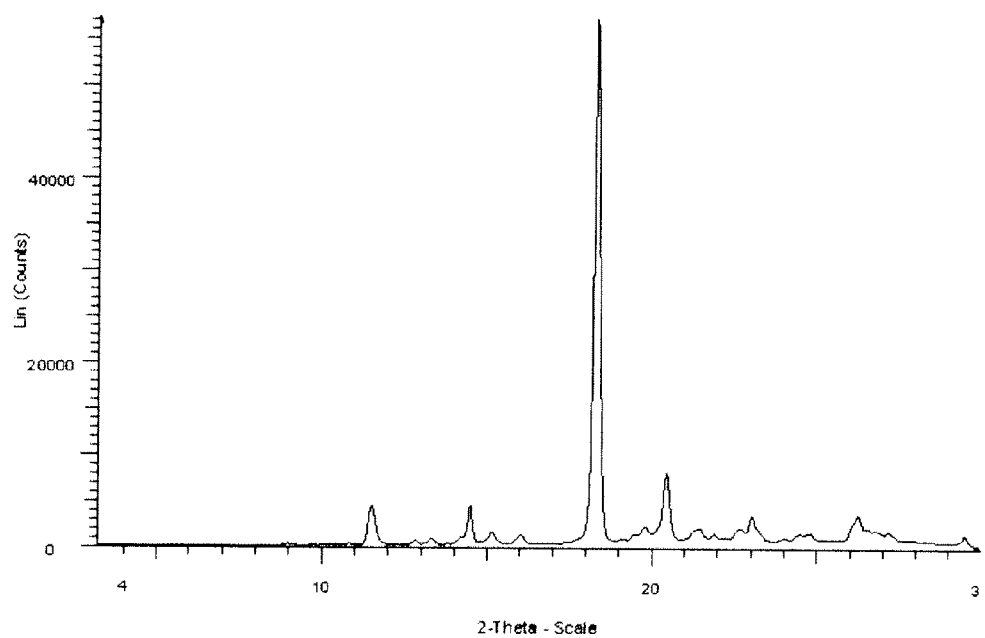
Fig. 2.6-A.

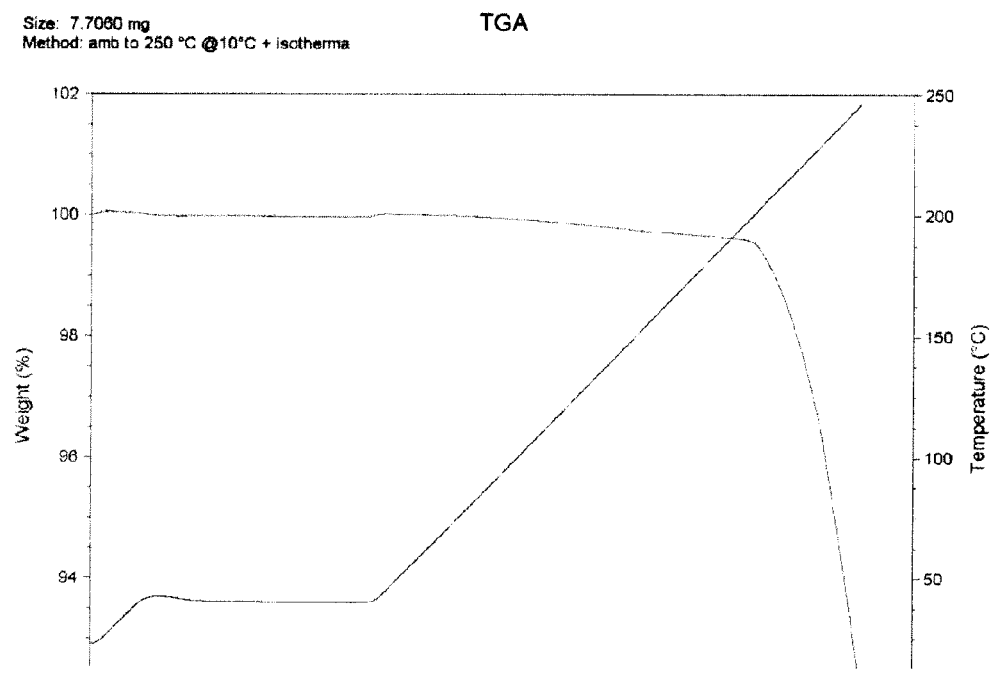
Fig. 2.6-B.

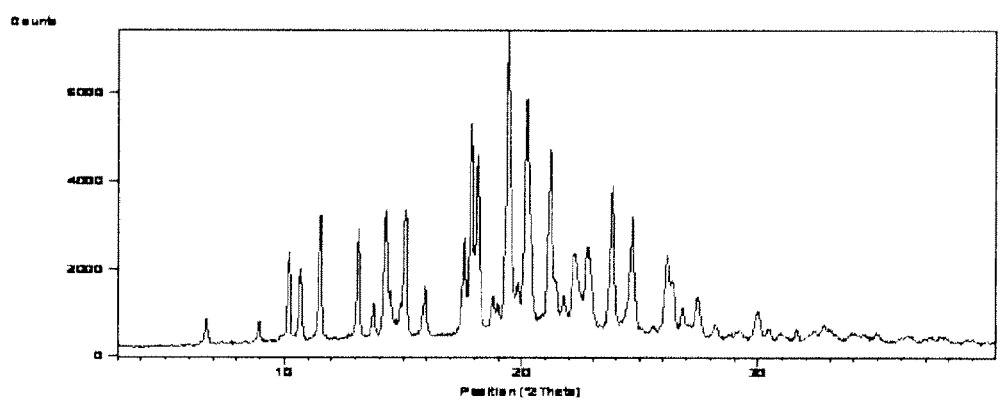
Fig. 3-A.

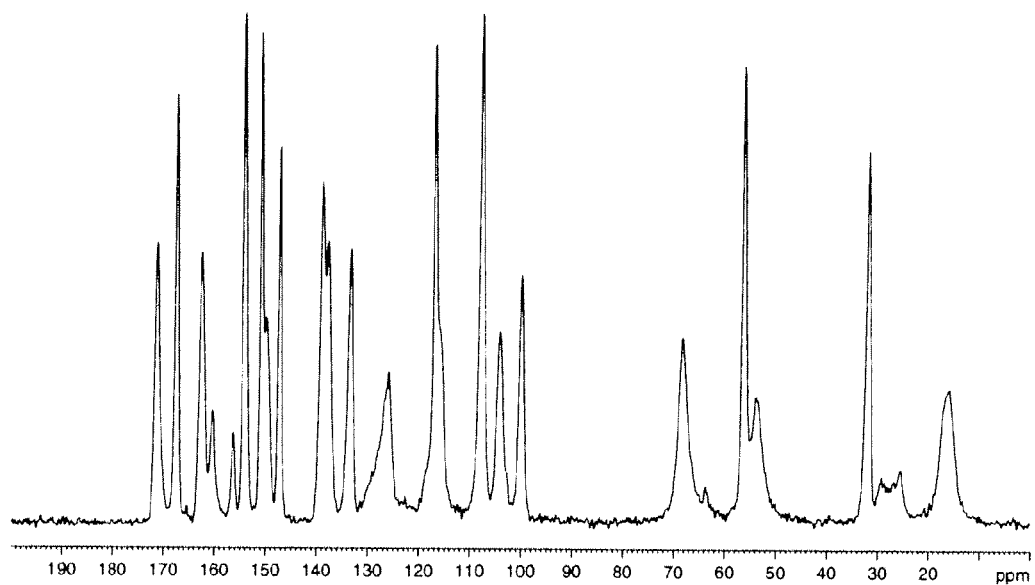
Fig. 3-B.

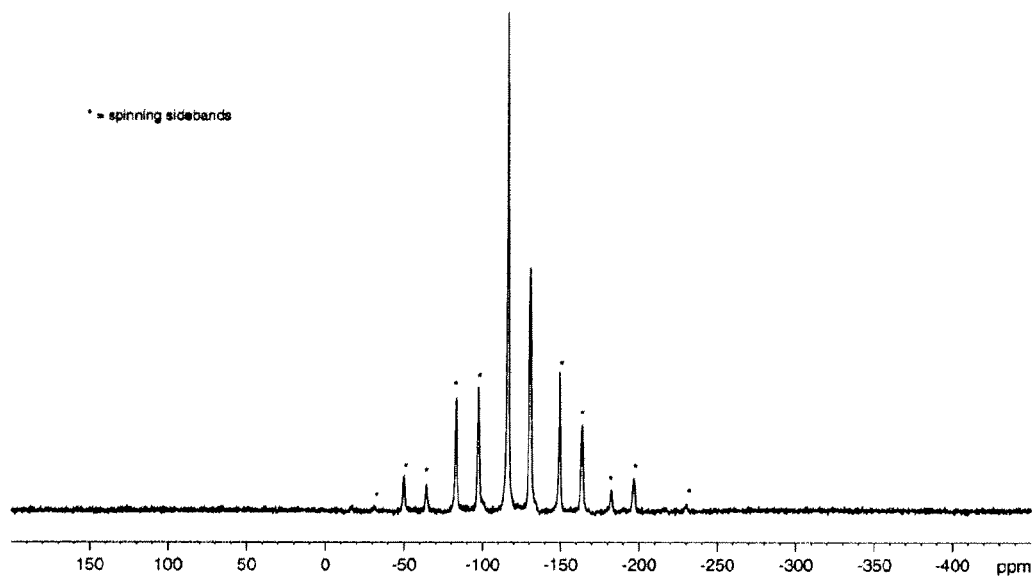
Fig. 3-C.

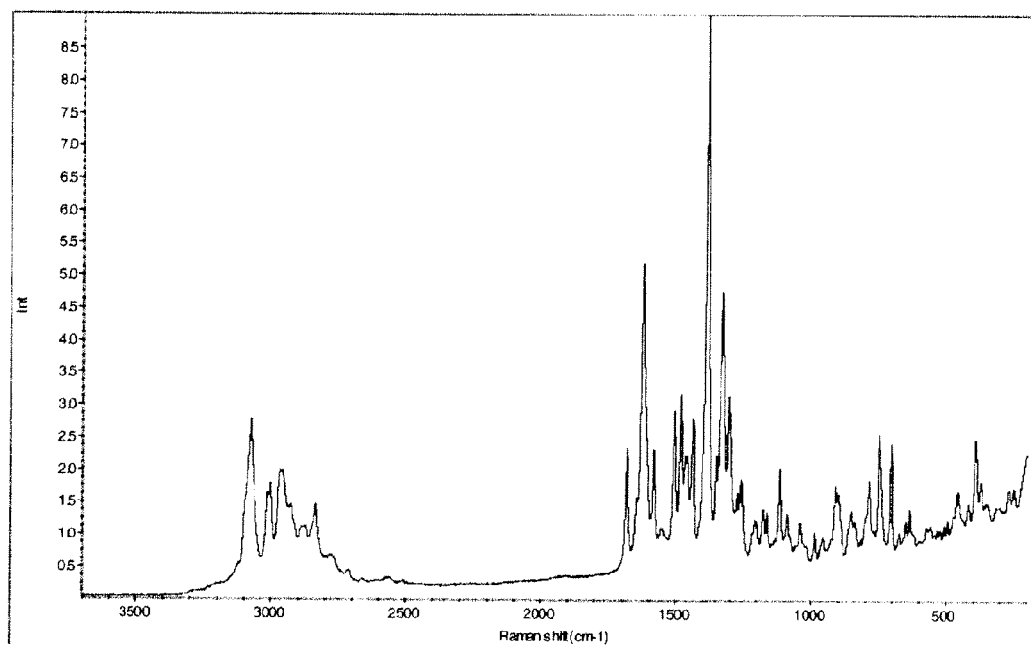
Fig. 3-D.

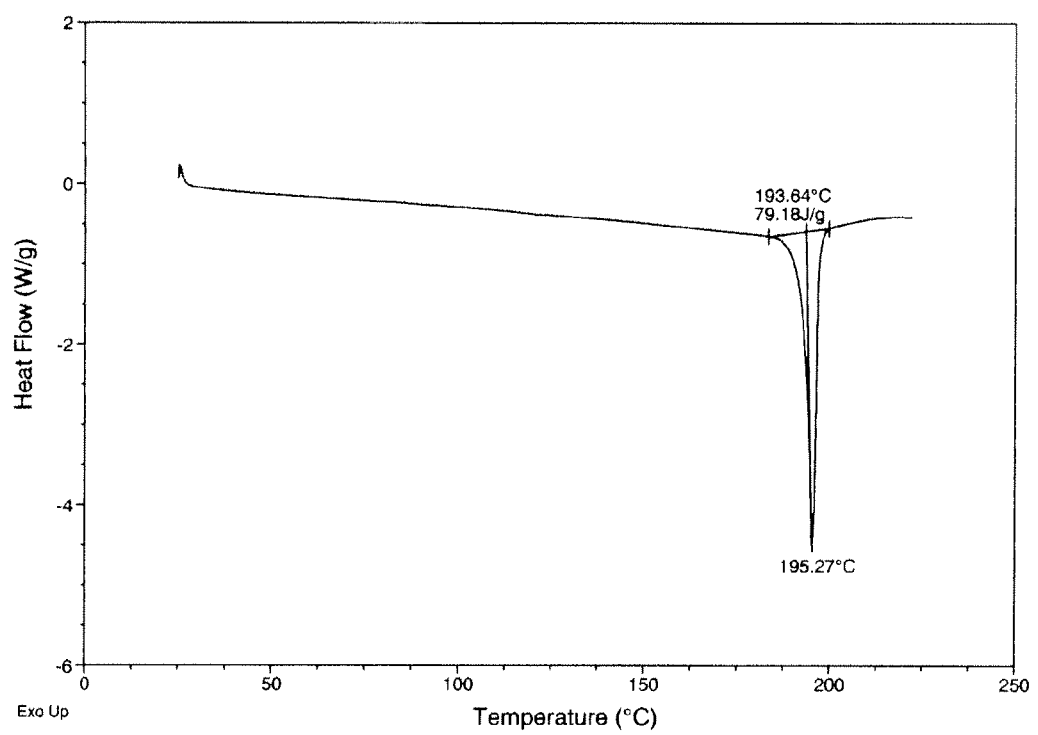
Fig. 3-E.

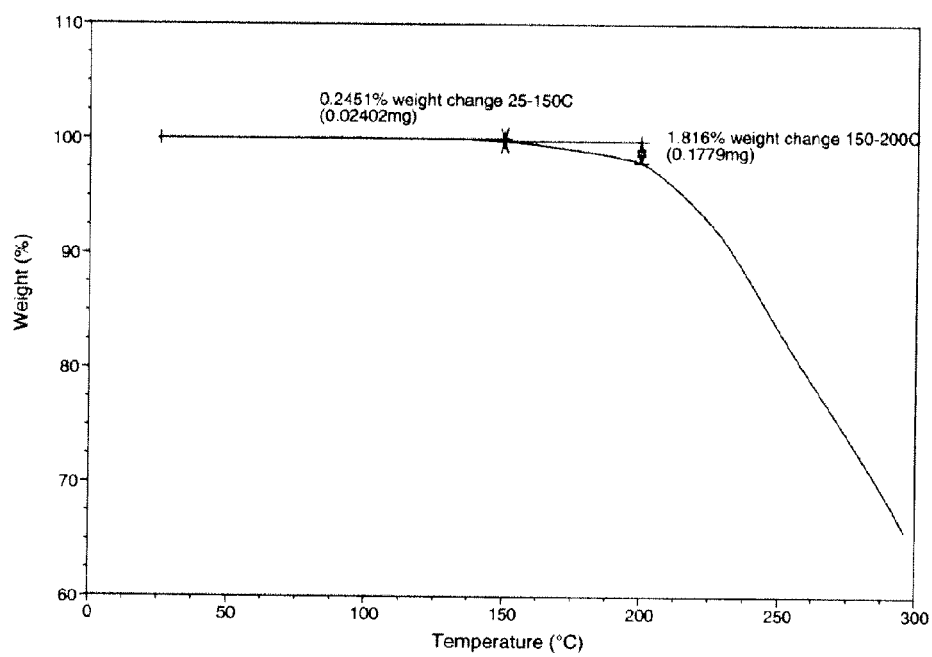
Fig. 3-F.

CRYSTALLINE FORMS ON N-[3-FLUORO-4-({6-(METHYLOXY)-7-[(3-MORPHOLIN-4-YLPROPYL)OXY]-QUINOLIN-4-YL}OXY)PHENYL]-N'-(4-FLUOROPHENYL)CYCLOPROPANE-1,1-DICARBOXAMIDE

CROSS-REFERENCE TO RELATED APPLICATIONS

This application is a United States National Phase filing of PCT/US2010/042353, filed Jul. 16, 2010, which claims priority to U.S. Provisional Application No. 61/226,509, filed Jul. 17, 2009, the entire contents of which are incorporated herein by reference.

FIELD OF THE INVENTION

This invention relates to crystalline forms of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide. The invention also relates to pharmaceutical compositions containing crystalline forms of the invention. The invention further relates to methods of treating cancer by inhibiting, regulating and/or modulating kinase signal transduction using crystalline N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide.

BACKGROUND OF THE INVENTION

Traditionally, dramatic improvements in the treatment of cancer are associated with identification of therapeutic agents acting through novel mechanisms. One mechanism that can be exploited in cancer treatment is the modulation of protein kinase activity, because signal transduction through protein kinase activation is responsible for many of the characteristics of tumor cells. Protein kinase signal transduction is of particular relevance in, for example, renal, gastric, head and neck, lung, breast, prostate, and colorectal cancers; hepatocellular carcinoma; as well as in the growth and proliferation of brain tumor cells.

Protein kinases can be categorized as receptor type or non-receptor type. Receptor-type tyrosine kinases are comprised of a large number of transmembrane receptors with diverse biological activity. For a detailed discussion of the receptor-type tyrosine kinases see Plowman et al., DN&P 7(6): 334-339, 1994. Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases, including, for example, immunological disorders, cardiovascular diseases, inflammatory diseases, and degenerative diseases. Therefore, protein kinases are attractive targets for small molecule drug discovery. Particularly attractive targets for small-molecule modulation with respect to antiangiogenic and antiproliferative activity include receptor type tyrosine kinases c-Met, KDR, c-Kit, Axl, flt-3, and flt-4.

The kinase c-Met is the prototypic member of a subfamily of heterodimeric receptor tyrosine kinases (RTKs) which include Met, Ron and Sea. The endogenous ligand for c-Met is the hepatocyte growth factor (HGF), a potent inducer of angiogenesis. Binding of HGF to c-Met induces activation of the receptor via autophosphorylation resulting in an increase of receptor dependent signaling, which promotes cell growth and invasion. Anti-HGF antibodies or HGF antagonists have been shown to inhibit tumor metastasis in vivo (See: Maulik et al Cytokine & Growth Factor Reviews 2002 13, 41-59). c-Met overexpression has been demonstrated on a wide variety of tumor types including breast, colon, renal, lung, squamous cell myeloid leukemia, hemangiomas, melanomas, astrocytomas, and glioblastomas. Additionally activating mutations in the kinase domain of c-Met have been identified in hereditary and sporadic renal papilloma and squamous cell carcinoma. (See, e.g., Maulik et al., Cytokine & growth Factor reviews 2002 13, 41-59; Longati et al., Curr Drug Targets 2001, 2, 41-55; Funakoshi et al., Clinica Chimica Acta 2003 1-23).

Inhibition of epidermal growth factor (EGF), vascular endothelial growth factor (VEGF) and ephrin signal transduction will prevent cell proliferation and angiogenesis, two key cellular processes needed for tumor growth and survival (Matter A., Drug Disc. Technol. 20016, 1005-1024). Kinase KDR (refers to kinase insert domain receptor tyrosine kinase) and flt-4 (fms-like tyrosine kinase-4) are both VEGF receptors. Inhibition of EGF, VEGF and ephrin signal transduction will prevent cell proliferation and angiogenesis, two key cellular processes needed for tumor growth and survival (Matter A. Drug Disc. Technol. 2001 6, 1005-1024). EGF and VEGF receptors are desirable targets for small molecule inhibition. All members of the VEGF family stimulate cellular responses by binding to tyrosine kinase receptors (the VEGFRs) on the cell surface, causing them to dimerize and become activated through transphosphorylation. The VEGF receptors have an extracellular portion having immunoglobulin-like domains, a single transmembrane spanning region and an intracellular portion containing a split tyrosine-kinase domain. VEGF binds to VEGFR-1 and VEGFR-2. VEGFR-2 is known to mediate almost all of the known cellular responses to VEGF.

Kinase c-Kit (also called stem cell factor receptor or steel factor receptor) is a type 3 receptor tyrosine kinase (RTK) belonging to the platelet-derived growth factor receptor subfamily. Overexpression of c-Kit and c-Kit ligand has been described in variety of human diseases including human gastrointestinal stromal tumors, mastocytosis, germ cell tumors, acute myeloid leukemia (AML), NK lymphoma, small-cell lung cancer, neuroblastomas, gynecological tumors and colon carcinoma. Moreover, elevated expression of c-Kit may also relate to the development of neoplasia associated with neurofibromatosis type 1 (NF-1), mesenchymal tumors GISTs and mast cell disease, as well as other disorders associated with activated c-Kit.

Kinase Flt-3 (fms-like tyrosine kinase-3) is constitutively activated via mutation, either in the juxtamembrane region or in the activation loop of the kinase domain, in a large proportion of patients with AML (Reilly, Leuk. Lymphoma, 2003, 44: 1-7).

Accordingly, small-molecule compounds that specifically inhibit, regulate, and/or modulate the signal transduction of kinases, particularly including c-Met, VEGFR2, KDR, c-Kit, Axl, flt-3, and flt-4 described above, are particularly desirable as a means to treat or prevent disease states associated with abnormal cell proliferation and angiogenesis. One such small-molecule is N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide, Compound (I), which has the chemical structure:

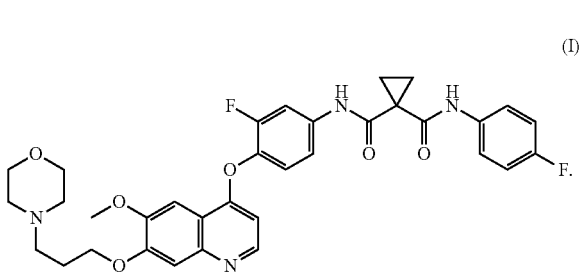 [SMILES: COc1cc2c(Oc3ccc(NC(=O)C4(C(=O)Nc5ccc(F)cc5)CC4)cc3F)ccnc2cc1OCCCN1CCOCC1]

(I)

WO 2005-030140 describes the synthesis of Compound (I) (Examples 25, 30, 36, 42, 43 and 44) and also discloses the therapeutic activity of this molecule to inhibit, regulate and/or modulate the signal transduction of kinases (Assays, Table 4, entry 312). Compound (I) has been measured to have a c-Met $IC_{50}$ value of about 0.6 nanomolar (nM). WO 2010/056960, which claims priority to U.S. provisional application 61/199,088, filed Nov. 13, 2008, describes a scaled-up synthesis of Compound (I).

Although therapeutic efficacy is the primary concern for a therapeutic agent, the solid-state form can be equally important to its development. Generally, the drug developer endeavors to discover a crystalline form that possesses desirable properties such as satisfactory water-solubility (including rate of dissolution), storage stability, hygroscopicity, formulatability, and reproducibility, all of which can impact the processability, manufacture, and/or bioavailability of the drug. Accordingly, discovery of one or more crystalline forms that possess some or all of these desired properties is vital to drug development.

SUMMARY OF THE INVENTION

This invention relates to crystalline forms of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide, Compound (I). The invention provides methods for treatment of cancer by exploiting the modulation of protein kinase activity. As discussed above, signal transduction through protein kinase activation is responsible for many of the characteristics of tumor cells. Protein kinase signal transduction is of particular relevance in, for example, renal (e.g. papillary renal cell carcinoma), gastric (e.g. metastatic gastric carcinoma), head and neck (e.g. squamous cell carcinoma), lung, breast, prostate, and colorectal cancers, squamous cell myeloid leukemia, hemangiomas, melanomas, astrocytomas, glioblastomas, hepatocellular carcinoma, hereditary and sporadic renal papilloma, as well as in the growth and proliferation of brain tumor cells.

Accordingly, the invention also relates to methods of treating cancer. These methods administer to a subject in need thereof therapeutically effective amounts of at least one crystalline form of Compound (I).

In another embodiment, the invention provides methods of treating diseases or disorders associated with uncontrolled, abnormal, and/or unwanted cellular activities. These methods comprise administering to a subject, in need thereof, therapeutically effective amounts of at least one crystalline form of Compound (I).

The invention further provides pharmaceutical compositions containing therapeutically effective amounts of at least one crystalline form of Compound (I) and a pharmaceutically acceptable excipient.

BRIEF DESCRIPTION OF THE FIGURES

FIG. 1-A shows the XRPD pattern for Compound (I) crystalline Form A from Example 1.1.1.

FIG. 1-B shows the XRPD pattern for Compound (I) crystalline Form A from Example 1.1.2.

FIG. 1-C shows the solid state $^{13}C$ NMR spectrum of Compound (I) crystalline Form A from Example 1.1.1.

FIG. 1-D shows the solid state $^{19}F$ NMR spectrum of Compound (I) crystalline Form A from Example 1.1.1.

FIG. 1-E shows the Raman spectrum of Compound (I) crystalline Form A from Example 1.1.1.

FIG. 1-F shows the DSC thermogram of Compound (I) crystalline Form A from Example 1.1.1.

FIG. 1-G shows the TGA thermogram of Compound (I) crystalline Form A from Example 1.1.1.

FIG. 1-H shows the sorption and desorption curves of the Gravimetric Vapor Sorption Study (GVS) of Compound (I) crystalline Form A from Example 1.1.2.

FIG. 2.1-A shows the XRPD pattern of Compound (I) crystalline Form B from Example 2.1.

FIG. 2.1-B shows the TGA thermogram of Compound (I) crystalline Form B from Example 2.1.

FIG. 2.6-A shows the XRPD pattern of Compound (I) crystalline Form C from Example 2.6.

FIG. 2.6-B shows the TGA thermogram of Compound (I) crystalline Form C from Example 2.6.

FIG. 3-A shows the XRPD pattern for Compound (I) crystalline Form B from Example 3.1.

FIG. 3-B shows the solid state $^{13}C$ NMR spectrum of Compound (I) crystalline Form B from Example 3.1.

FIG. 3-C shows the solid state $^{19}F$ NMR spectrum of Compound (I) crystalline Form B from Example 3.1.

FIG. 3-D shows the Raman spectrum of Compound (I) crystalline Form B from Example 3.1.

FIG. 3-E shows the DSC thermogram of Compound (I) crystalline Form B from Example 3.1.

FIG. 3-F shows the TGA thermogram of Compound (I) crystalline Form B from Example 3.1.

DETAILED DESCRIPTION OF THE INVENTION

Crystalline Forms of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide, Compound (I)

The invention relates to crystalline forms of Compound (I). The Examples below describe these crystalline forms Compound (I) according to the invention including their preparation and characterization. These are non-solvated crystalline forms.

The solid state of a compound can be characterized by various physical properties such as solubility, melting point, x-ray powder diffraction, solid state NMR spectroscopy, and Raman spectroscopy. The different crystalline forms of Compound (I) can be identified, or characterized, one from the other by comparing their respective analytical data, such as their XRPD patterns or solid state NMR peaks. A comparison of the XRPD patterns for Forms A, B and C suggests the listing of characteristic peaks for each form as listed in Table 1. Each form may be characterized by this set of characteristic peaks or a subset thereof. Low angle XRPD peaks, below about 20°2θ, are often preferred to characterize a crystalline solid. Additional data for each crystalline form which may be used to identify each particular form is presented in the Examples below.

TABLE 1

Characteristic XRPD Peaks for Crystalline Forms of Compound (I), °2θ ± 0.2 °2θ

| Form A | Form B | Form C |
|---|---|---|
| 7.2 | 6.7 | 11.5 |
| 7.7 | 10.2 | 14.5 |
| 12.5 | 13.1 | 18.3 |
| 15.5 | 22.2 | 20.4 |
| 16.5 | | |
| 17.1 | | |
| 19.1 | | |
| 23.5 | | |
| 25.4 | | |
| 25.7 | | |
| 29.0 | | |

Crystalline forms of Compound (I) disclosed here may possess advantages vis-á-vis each other and other forms. Such advantages may suggest the use of one form for a particular formulation or processing, or as an intermediate. As one example of a difference, forms A and B are enantiotropically related. Form A is believed to be the most thermodynamically stable form at temperatures less than about 75° C. Form B is believed to be the most thermodynamically stable form at temperatures greater than about 75° C. This difference in thermodynamic stability can inform the choice of processing conditions in the manufacturing process for a pharmaceutical formulation of crystalline Compound (I).

The invention also relates to a method of preparing crystalline N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide Form A comprising the steps of: dissolving N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide in hot n-propanol to form a solution; cooling the solution sufficiently to afford precipitation of the crystalline form; and isolating the crystalline form.

The invention further relates to a method of preparing the crystalline form of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide Form B comprising the steps of: adding sufficient heptane to an isopropanol-containing solution of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide at an elevated temperature to precipitate the crystalline form; cooling the mixture under conditions sufficient to further precipitate the crystalline form; and isolating the crystalline form. An isopropanol-containing solution is a solution containing isopropanol in an amount of at least 10% by volume.

The invention also relates to a method of preparing crystalline N-[3-fluoro-4-({6-(methyloxy)-7-[(3-morpholin-4-ylpropyl)oxy]quinolin-4-yl}oxy)phenyl]-N-(4-fluorophenyl)cyclopropane-1,1-dicarboxamide Form C comprising the steps of: dissolving N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide in methanol to form a solution; allowing the solution to stand under conditions sufficient to precipitate the crystalline form; and isolating the crystalline form.

Methods of Treatment

As discussed above, Compound (I) possesses beneficial therapeutic properties in its ability to specifically inhibit, regulate and/or modulate the signal transduction of kinases, particularly including c-Met, KDR, c-Kit, Axl, flt-3, and flt-4. This makes Compound (I) particularly desirable as a therapeutic to treat and/or prevent disease states associated with abnormal cell proliferation and angiogenesis.

The invention therefore provides methods for treatment and/or prevention of cancer by exploiting the modulation of protein kinase activity. As discussed above, signal transduction through protein kinase activation is responsible for many of the characteristics of tumor cells. Protein kinase signal transduction is of particular relevance in, for example, renal (e.g. papillary renal cell carcinoma), gastric (e.g. metastatic gastric carcinoma), head and neck (e.g. squamous cell carcinoma), lung, breast, prostate, and colorectal cancers, squamous cell myeloid leukemia, hemangiomas, melanomas, astrocytomas, glioblastomas, hepatocellular carcinoma, hereditary and sporadic renal papilloma, as well as in the growth and proliferation of brain tumor cells.

Accordingly, the invention relates to a method of treating and/or preventing cancer. The method comprises administering to a subject, in need thereof, a therapeutically effective amount of crystalline N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide, Compound (I), according to the invention. The crystalline Compound (I) may be in any of the crystalline forms of the invention and mixtures thereof. The subject to be treated is generally a mammal and most often a human. The cancer being treated is preferably one discussed above, such as renal cancer, gastric cancer, head and neck cancer, lung cancer, breast cancer, prostate cancer, colorectal cancer, squamous cell myeloid leukemia, hemangiomas, melanomas, astrocytomas, glioblastomas, hereditary and sporadic renal papilloma, squamous cell carcinoma, and brain tumors but may be any form of cancer for which crystalline forms of Compound (I) according to the invention have efficacy.

In another embodiment, the invention provides a method of treating and/or preventing diseases or disorders associated with uncontrolled, abnormal, and/or unwanted cellular activities. This method administers, to a subject in need thereof, a therapeutically effective amount of a crystalline form of Compound (I).

Pharmaceutical Compositions of the Invention

The invention relates to pharmaceutical compositions comprising a therapeutically effective amount of at least one crystalline form of N-[3-fluoro-4-({6-(methyloxy)-7-[(3-morpholin-4-ylpropyoxy]quinolin-4-yl}oxy)phenyl]-N'-(4-fluorophenyl)cyclopropane-1,1-dicarboxamide, Compound (I), according to the invention and at least one pharmaceutically acceptable carrier, (also known as a pharmaceutically acceptable excipient). As discussed above, the crystalline forms of Compound (I) are therapeutically useful for the treatment and/or prevention of disease states associated with abnormal cell proliferation and angiogenesis. The crystalline forms of Compound (I) possess therapeutic activity to inhibit, regulate and/or modulate the signal transduction of kinases such as described in WO2005/030140. Pharmaceutical compositions for the treatment of those disease states contain a therapeutically effective amount of at least one crystalline form of Compound (I) according to the invention to inhibit, regulate and/or modulate the signal transduction of kinases as appropriate for treatment of a patient with the particular disease. A pharmaceutical composition of the invention may be in any pharmaceutical form which contains a crystalline form of Compound (I) according to the invention. The pharmaceutical composition may be, for example, a tablet, capsule, liquid suspension, injectable, topical, or transdermal. The pharmaceutical compositions generally contain about 1% to about 99% by weight of at least one crystalline form of Compound (I) of the invention and 99% to 1% by weight of a suitable pharmaceutical excipient. In one example, the composition will be between about 5% and about 75% by weight of a crystalline form of Compound (I) of the invention, with the remainder of the composition being suitable pharmaceutical excipients or other adjuvants, as discussed below.

A "therapeutically effective amount of a crystalline form of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide" according to the invention sufficient to inhibit, regulate and/or modulate the signal transduction of kinases" (discussed here concerning the pharmaceutical compositions) refers to any amount sufficient to treat a patient suffering from any of a variety of cancers associated with abnormal cell proliferation and angiogenesis. The actual amount required for treatment of any particular patient will depend upon a variety of factors including the disease state being treated and its severity; the specific pharmaceutical composition employed; the age, body weight, general health, sex and diet of the patient; the mode of administration; the time of administration; the route of administration; and the rate of excretion of the crystalline form of Compound (I) according to the invention; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001. The crystalline forms of Compound (I) according to the invention, and pharmaceutical compositions containing them, may be used in combination with anticancer or other agents that are generally administered to a patient being treated for cancer. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. For a pharmaceutical composition of the invention, that is, one containing a crystalline form of Compound (I) of the invention, a carrier should be chosen so as to substantially maintain the particular crystalline form of Compound (I) of the invention. In other words, the carrier should not substantially alter the crystalline form of the compound (I) of the invention. Nor should the carrier be otherwise incompatible with the crystalline form of Compound (I) according to the invention, such as by producing any undesirable biological effect or otherwise interacting in a deleterious manner with any other component(s) of the pharmaceutical composition.

The pharmaceutical compositions of the invention may be prepared by methods known in the pharmaceutical formulation art, for example, see Remington's Pharmaceutical Sciences, 18th Ed., (Mack Publishing Company, Easton, Pa., 1990). In solid dosage forms, at least one crystalline form of Compound (I) may be admixed with at least one pharmaceutically acceptable excipient such as sodium citrate or dicalcium phosphate or any other excipients known to those of skill in the art, such as: (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Solid dosage forms as described above can be prepared with coatings and shells, such as enteric coatings and others well known in the art. They may contain opacifying agents, and can also be of such composition that they release the active compound or compounds in a certain part of the intestinal tract in a delayed manner. Examples of embedded compositions that can be used are polymeric substances and waxes. The active compounds, at least one crystalline form of Compound (I), can also be in microencapsulated form, if appropriate, with one or more of the above-mentioned excipients.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the invention with, for example, suitable non-irritating excipients or carriers such as cocoa butter, polyethyleneglycol or a suppository wax, which are solid at ordinary temperatures but liquid at body temperature and therefore, melt while in a suitable body cavity and release the active compound therein.

Because the crystalline forms of Compound (I) of the invention are maintained during their preparation, solid dosage forms are preferred for the pharmaceutical composition of the invention. Solid dosage forms for oral administration, which includes capsules, tablets, pills, powders, and granules, are particularly preferred. In such solid dosage forms, the active compound is mixed with at least one inert, pharmaceutically acceptable excipient. Administration of a crystalline form of Compound (I) in pure form, or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semisolid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. One preferable route of administration is oral administration, using a convenient dosage regimen that can be adjusted according to the degree of severity of the disease-state to be treated.

EXAMPLES

Example 1

Preparation and Physical Characterization of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide Crystalline Form A, Compound (I)

1.1 Preparation of Compound (I) Crystalline Form A.

1.1.1 n-Propanol Method:

N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide (1.01258 g) was combined with 10 mL of n-propanol. The mixture was heated to 90° C. and stirred for 2 hours (h), resulting in a clear solution. The hot solution was filtered with a 0.2 µm nylon filter. The filtrate (1 mL) was transferred to a 4-mL screw-cap vial equipped with a stir bar. The sample was sealed, placed on a stir plate, and allowed to stir overnight at room temperature, (approximately 23° C.), during which time a precipitate formed. The precipitate was designated Crystalline Form A of the Compound (I).

1.1.2 Bisphosphate Salt Method

N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide free base was dissolved in acetone (46.0 L) and water (12.0 L). Phosphoric acid (85%, 1.2 L) was added at a rate such that the batch temperature did not exceed 30° C. The batch was maintained at approximately 15-30° C. with stirring for 1 h during which time the product precipitated. The solids were collected by filtration, washed with acetone and dried at approximately 60° C. under vacuum to afford N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide bisphosphate (5.5 kg).

100 g of the bisphosphate salt of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide was dissolved in 500 mL (5 vol.) of water. The aqueous solution pH was then adjusted from pH of about 2 to a pH of about 10 using 10% aqueous potassium carbonate. The resultant free base was filtered and allowed to air dry overnight. The solid free base was further dried at 40° C. for 4 h. 78.58 g of the free base was recovered. A $^1$H NMR spectrum of the recovered free base showed it was impure. The free base was further investigated. About 5 g of the free base was dissolved in 500 mL of ethyl acetate. The organic layer was washed twice with 200 mL of water. The organic layer was split into two equal portions. One portion, A, was dried over magnesium sulfate and reduced in volume to dryness. The other portion, B, was washed with 100 mL of 1N aqueous sodium hydroxide and the layers separated. The organic layer of portion B was dried over magnesium sulfate and reduced to solid in vacuo. $^1$H NMR of the portion B residue showed it to be the free base. The remaining free base solid from portion A was then dissolved in ethyl acetate and washed with 1N aqueous sodium hydroxide and the layers separated. The organic layer was dried over magnesium sulfate and reduced to dryness in vacuo. The solid free base was dissolved in acetone and rapidly precipitated out upon addition of heptane. The solid free base was then filtered and dried. The total solid recovered was 37.6 g. The recovered solid was shown to be Compound (I) Crystalline Form A.

1.2 X-ray Powder Diffraction Characterization of Compound (I) Crystalline Form A.

The X-ray powder diffraction pattern of Compound (I) crystalline Form A prepared in Example 1.1.1 was acquired using a PANalytical X'Pert Pro diffractometer. Samples were gently flattened onto a zero-background silicon insert sample holder. A continuous 2θ scan range of 2° to 50° was used with a Cu Kα radiation source and a generator power of 40 kV and 45 mA. A 2θ step size of 0.017 degrees/step with a step time of 40.7 seconds was used. Samples were rotated at 30 rpm. Experiments were performed at room temperature and at ambient humidity. FIG. 1-A shows the XRPD pattern for N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide crystalline Form A from Example 1.1.1. The following peaks at an experimental °2θ+0.1°2θ identified in the XRPD pattern: 7.2, 7.7. 9.7, 10.8, 12.5, 14.1, 14.9, 15.2, 15.5, 16.0, 16.5, 17.1, 17.5, 17.8, 19.1, 19.4, 20.0, 20.4, 20.7, 22.8, 23.5, 25.4, 25.7, 27.5, 29.0, 29.6, 30.0, 30.3, 32.3. Table 1, above, lists peaks at °2θ+0.2° 2θ which characterize Form (A). The entire list of peaks indentified in the XRPD pattern or listed in Table 1, or a subset thereof, may be sufficient to characterize Form (A) of Compound (I).

X-ray powder diffraction for crystalline N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide prepared in Example 1.1.2 was carried out on a Bruker C2 diffractometer equipped with an XYZ stage and laser video microscope for auto-sample positioning; and a HiStar area Detector with typical collection times of 120 s. The sealed copper tube (Cu Kα radiation; 1.5406 Å) voltage and amperage were set at 40 kV and 40 mA. The X-ray optics on the C2 consists of a single Göbel mirror coupled with a pinhole collimator of 0.3 mm. Beam divergence i.e., effective size of X-ray spot, gives a value of approximately 4 mm. Theta-theta continuous scans were employed with a sample-detector distance of 20 cm which gives an effective 2 theta range of 3.2-29.8°. A corundum (α-Al$_2$O$_3$) standard (NIST 1976 flat plate) was run weekly to check the instrument calibration. Sample preparation consisted of 1-2 mg of sample pressed lightly on a glass slide to obtain a flat surface. FIG. 1-B shows the XRPD pattern of Compound (I) crystalline Form A from Example 1.1.2. The pattern in FIG. 1-B is broadened in comparison to that in FIG. 1-A because of a lesser degree of crystallinity in this sample.

1.3 $^{13}$C and $^{19}$F Solid-State NMR Spectra of Compound (I) Crystalline Form A.

Solid-state NMR spectra of Compound (I) crystalline Form A prepared in Example 1.1.1 were acquired using a Bruker Avance 400 triple-resonance spectrometer operating at a $^1$H frequency of 399.87 MHz. $^{13}$C NMR spectra were obtained using a cross-polarization pulse sequence with a Bruker 4-mm triple resonance magic-angle spinning probe at a rotor frequency of 8 kHz. A linear power ramp from 75 to 90 kHz was used on the $^1$H channel to enhance cross-polarization efficiency. Spinning sidebands were eliminated by a five-pulse total sideband suppression pulse sequence. $^{19}$F spectra were obtained using the same spectrometer and probe, using a cross-polarization pulse sequence and spinning at a rotor frequency of 12.5 kHz. FIG. 1-C shows the solid state $^{13}$C NMR spectrum of Compound (I) crystalline Form A prepared in Example 1.1.1. The $^{13}$C NMR peak positions are reported relative to tetramethylsilane at 0 ppm (parts per million) and are quoted to a precision of +/−0.2 ppm, because of instrumental variability and calibration. The following peaks were identified in the solid state $^{13}$C NMR spectrum: 172.0, 168.2, 161.2, 158.6, 156.8, 154.3, 153.3, 150.6, 150.1, 146.5, 138.9, 136.0, 132.6, 128.6, 127.4, 124.9, 118.1, 116.5, 114.8, 108.3, 106.2, 102.5, 99.1, 66.8, 57.3, 55.3, 52.8, 50.7, 28.5, 19.4, 14.6. Characteristic peaks for Form A from the solid state $^{13}$C NMR spectra include those at 161.2, 158.6, 153.3, 146.5, 136.0, 132.6, 128.6, 127.4, and 124.9 ppm±0.2 ppm or a subset thereof. FIG. 1-D shows the solid state $^{19}$F NMR spectrum of Compound (I) crystalline Form A prepared in Example 1.1.1. The peaks marked with an asterisk (*) are spinning side bands. The solid state $^{19}$F NMR spectrum showed peaks −116.8 and −128.6 relative to $CFCl_3$ and with a precision of ±0.2 ppm, because of instrumental variability and calibration. Both solid state $^{19}$F NMR peaks are considered to be characteristic of Form A.

1.4 Raman Spectrum of Compound (I) Crystalline Form A.

The Fourier-transform (FT) Raman spectrum of Compound (I) crystalline Form A prepared in Example 1.1.1 was acquired using a Thermo Nicolet 960 spectrometer equipped with a liquid nitrogen-cooled germanium detector and a motorized stage accessory with video control. A 1.064 μm laser was used with a power setting of 0.55 W. The powdered sample was placed onto a glass microscope slide and placed directly into the beam using the stage. A 1-mm laser spot size was used, and 512 scans were collected at 2 cm$^{-1}$ resolution. The FT-Raman spectrum of crystalline Form A of Compound (I) is shown in FIG. 1-E. The following peaks (Raman shift, cm$^{-1}$+/−2 cm$^{-1}$) were observed in the FT Raman spectrum: 218, 258, 370, 384, 456, 480, 571, 636, 649, 712, 751, 784, 801, 835, 870, 891, 969, 981, 1024, 1051, 1081, 1118, 1155, 1208, 1250, 1264, 1308, 1327, 1389, 1404, 1433, 1454, 1479, 1506, 1552, 1584, 1623, 1694, 2804, 2831, 2862, 2952, 3018, 3088, 3096. These peaks or a subset thereof may be used to identify crystalline Form A of Compound (I).

1.5 Thermal Characterization of Compound (I) Crystalline Form A.

DSC thermograms were acquired using a TA Instruments Q2000 Differential Scanning calorimeter. A sample mass of 1.5360 mg of Compound (I) crystalline Form A prepared in Example 1.1.1 was weighed out directly into an aluminum DSC pan. The pan was sealed by applying pressure by hand and pushing each part the pan together (also known as a loose lid configuration). The temperature was ramped from 25° C. to 225° C. at 10° C./minute. A peak melting temperature of 180.4° C. and a heat flow of 92.65 J/g was measured for the melting endotherm. The DSC thermogram is shown in FIG. 1-F. Exothermic events are plotted in the upward direction.

TGA thermograms were acquired using a TA Instruments Q500 Thermogravimetric Analyzer. The sample pan was tared, and 10.7750 milligrams of Compound (I) crystalline Form A prepared in Example 1.1.1 was placed in the pan. The temperature was ramped from 25° C. to 300° C. at 10° C./minute. A weight loss of 0.02% was observed up to 150° C., with an additional weight loss of 1.02% up to 180° C., most likely from decomposition. The TGA thermogram is shown in FIG. 1-G.

1.6 Stability Studies of Compound (I) Crystalline From A

Gravimetric Vapor Sorption (GVS) and Karl Fisher Water Content Determination studies were down using crystalline N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide prepared in Example 1.1.2.

Gravimetric Vapor Sorption Study (GVS):

The GVS study was run using a standard procedure. Samples were run on a Hiden IGASorp moisture sorption analyzer running CFRSorp software. Sample sizes were typically 10 mg. A moisture adsorption desorption isotherm was performed as outlined below. All samples were loaded/unloaded at typical room humidity and temperature (40% RH, 25° C.) and analyzed afterwards by XRPD. The standard isotherm run is a cycle starting at 40% RH→90%→Dry finishing at 35% RH at 25° C. and 10% RH intervals. The crystalline Compound (I) prepared in Example 1.1.2 showed a 0.5% weight gain at 25° C. and 90% humidity, reanalysis of the sample by XRPD showed no change in form. The GVS sorption and desorption curves are shown in FIG. 1-H.

Karl Fisher Water Determination:

The study was done using a standard procedure. Water contents were measured on a Mettler Toledo DL39 Coulometer using Hydranal AG Oven reagent and an argon purge. Samples were introduced into the vessel as solids weighed out onto a platinum TGA pan which was connected to a subaseal via tweezers to avoid water ingress. Approximately 10 mg of sample was used per titration and each analysis was performed in duplicate. The water content of crystalline Compound (I) prepared in Example 1.1.2 was measured in duplicate and gave an average value of 0.1%.

Example 2

Additional Preparations of Crystalline N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide, Compound (I)

2.1-2.8. Preparations of Crystalline Compound (I), Forms B and C.

Crystalline forms of Compound (I) were prepared using the solvents listed in Table 2. Approximately 100 mg of amorphous Compound (I) was placed in a 4-mL screw cap vial and 10 volumes of a potential solvent was added. If dissolution was not achieved on shaking, the vial was heated. If dissolution was still not achieved a further 10 volumes of solvent was added and the mixture shaken and heated. The solutions were left for 48 h at room temperature then inspected for precipitation. If no solid was present, the screw cap was loosened to allow for solvent evaporation. All solids were examined in situ by polarized light microscopy and where sufficient material was available after harvesting and crushing of large particles, by XRPD. The results which are shown in Table 2 reveal a number of suitable solvents for preparing crystalline forms of Compound (I).

TABLE 2

| Example | Solvent | Dissolved in 10 vols. | Form |
| --- | --- | --- | --- |
| 2.1 | Acetonitrile | | B |
| 2.2 | n-Butanol | Hot | B* |
| 2.3 | Ethyl acetate | Cold | B |
| 2.4 | Ethanol | Cold | B |
| 2.5 | i-Propyl acetate | Cold | B |
| 2.6 | Methanol | Cold | C |
| 2.7 | Methyl isobutyl ketone (MIBK) | Cold | B |
| 2.8 | Toluene | Cold | B* |

*Samples obtained from this procedure were poorly crystallized relative to other samples of Form B.

2.9 Characterization of Crystalline Form B in 2.1 and Crystalline Form C in 2.6

X-ray Powder Diffraction (XRPD): X-ray powder diffraction was carried out on a Bruker C2 diffractometer equipped with an XYZ stage and laser video microscope for auto-sample positioning and a HiStar area Detector with typical collection times of 120 s. The sealed copper tube (Cu Kα radiation; 1.5406 Å) voltage and amperage were set at 40 kV and 40 mA. The X-ray optics on the C2 consists of a single Göbel mirror coupled with a pinhole collimator of 0.3 mm. Beam divergence i.e., effective size of X-ray spot, gives a value of approximately 4 mm. Theta-theta continuous scans were employed with a sample-detector distance of 20 cm which gives an effective 2 theta range of 3.2-29.8°. A corundum (α-$Al_2O_3$) standard (NIST 1976 flat plate) was run weekly to check the instrument calibration. Sample preparation consisted of 1-2 mg of sample pressed lightly on a glass slide to obtain a flat surface. FIGS. 2.1-A and 2.6-A show the XRPD pattern of crystalline Form B from acetonitrile, 2.1, and of crystalline Form C, 2.6, above respectively. The following peaks at an experimental °2θ±0.2±°2θ were identified in the XRPD pattern: 11.5, 14.5, 15.1, 18.3, 19.8, 20.4, 21.4, 22.7, 23.1, 26.3, 26.8, and 27.2. Table 1, above, lists peaks at °2θ+0.2°2θ which characterize Form C as shown in FIG. 2.6-A. The entire list of peaks indentified in the XRPD pattern or listed in Table 1, or a subset thereof, may be sufficient to characterize crystalline Form C of Compound (I). FIGS. 2.1-B and 2.6-B show the TGA thermograms of crystalline Form B from acetonitrile and of crystalline Form C from methanol, above respectively.

Thermogravimetric analysis (TGA) data was collected on a TA Instruments Q500 TGA, calibrated with Alumel and running at a scan rate of 10° C./minute. A nitrogen purge at 60 mL/min was maintained over the sample. The sample was loaded onto a pre-tared platinum crucible. The specific TGA acquisition method is noted on FIGS. 2.1-B and 2.6-B. FIG. 2.1-B shows the TGA thermogram of crystalline Form B from acetonitrile, 2.1, using an 18.1 mg sample with a temperature range from ambient to 350° C. FIG. 2.6-B shows the TGA thermogram of crystalline Form C, 2.6, using a 7.71 mg sample with a temperature range from ambient to 250° C.

Example 3

Further Preparation and Characterization of Crystalline N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide, Compound (I), Form B 3.1: Preparation of Compound (I), Crystalline Form B.

To a dried reactor (reactor 1) was added 1-(4-fluorophenyl carbamoyl)cyclopropane carboxylic acid (21.5 kg), THF (76 kg), and N,N-dimethylformamide (DMF, 0.09 kg) which was agitated at 20° C. until dissolved. The contents of the reactor were cooled to about 15° C. and oxalyl chloride (12.7 kg) was added over 38 min while keeping the internal temperature in the reactor below 20° C. When the addition was complete, the transfer line was rinsed with THF (3 kg) which was added into the reactor. After 1 h at about 20° C., an additional 0.6 kg of oxalyl chloride and 2 kg of THF were added to the reactor. This process of adding additional oxalyl chloride (0.6 kg) and THF (2 kg) was repeated a second time, and then a third time at lesser amounts of oxalyl chloride (0.13 kg) with THF (2 kg).

To a separate reactor (reactor 2) was added water (60 L), $K_2CO_3$ (11.1 kg), 3-fluoro-4-[(6-(methyloxy)-7-{[3-(4-morpholinyl)propyl]oxy}-4-quinolinyl)oxy]phenyl}amine (32.5 kg, see CAS Reg. No. 479690-10-3 and US 2004/0242603) and THF (177 kg) and the reactor contents were adjusted to about 15° C. The contents of reactor 1 were added to reactor 2 while maintaining the temperature in reactor 2 at less than 20° C. Reactor 1 was rinsed with THF (5 kg) which was transferred to reactor 2 and the temperature of the contents of reactor 2 was adjusted to about 20° C. After about 3 h, 171 kg of 0.8 M aqueous $K_2CO_3$ and isopropyl acetate (119 kg) were added, the mixture was stirred for 10 min, settled and the lower aqueous layer was discarded. An additional 171 kg of 0.8 M aqueous $K_2CO_3$ was added, mixed, settled and the aqueous layer again discarded. Water (137 kg) was added, mixed, settled and the aqueous layer again discarded. Steam activated powdered carbon (Darco G-60 from Norit Americas, Inc.) (3.4 kg) and isopropyl acetate (3 kg) were added, stirred for about 2.5 h then transferred through a filter containing diatomaceous earth into a separate reactor (reactor 3). Reactor 2 was rinsed twice with isopropyl acetate (33 kg each) which was sent through the filter above and combined with the batch contained in reactor 3. The contents of reactor 3 were concentrated to a final volume of about 104 L under vacuum while keeping the temperature less than 50° C. Isopropanol (161 kg) was added and again the contents of reactor 3 were concentrated to a final volume of about 104 L under vacuum while keeping the temperature less than 50° C. Isopropanol (161 kg) was again added and the contents of reactor 3 were concentrated to a final volume of about 100 L under vacuum while keeping the temperature less than 50° C. The contents of reactor 3 were warmed to about 75° C., held for about 80 min, and cooled to about 55° C. Heptane (1 kg) mixed with about 1% isopropanol was added to the reactor while at about 55° C. and the batch was held about 70 min until crystallization was observed. Heptane mixed with about 1% isopropanol (46 kg) was added to the reactor while keeping the reactor contents at about 55° C. and the reactor contents were held an additional 75 min at this temperature. The reactor contents were cooled to about 20° C. over about 5 h and held at this temperature for an additional about 12 h. The reactor contents were cooled to about 5° C. and held at this temperature for about 1 h. The contents of reactor 3 were transferred to a filter dryer and rinsed with a mixture of isopropanol (18 kg) and heptane (8 kg). The contents of the filter dryer were dried at about 50° C. over about 56 h to yield 42.8 kg (89%) of Compound (I) Crystalline Form B as an off-white powder.

3.2 X-Ray Powder Diffraction Characterization of Compound (I) Crystalline Form B.

X-ray powder diffraction patterns were acquired using a PANalytical X'Pert Pro diffractometer. Samples were gently flattened onto a zero-background silicon insert sample holder. A continuous 2θ scan range of 2° to 50° was used with a CuKα radiation source and a generator power of 40 kV and 45 mA. A 2θ step size of 0.017 degrees/step with a step time of 40.7 seconds was used. Samples were rotated at 30 rpm. Experiments were performed at room temperature and at ambient humidity. FIG. 3-A shows the XRPD pattern for N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide crystalline Form B from Example 3.1. The following peaks at an experimental °2θ±0.1°2θ were identified in the XRPD pattern: 6.7, 9.9, 10.2, 10.7, 11.5, 13.1, 14.3, 15.1, 15.9, 17.6, 17.9, 18.2, 19.4, 20.2, 21.2, 22.2, 22.8, 23.8, 24.7, 26.2, 27.5, and 30.0. Table 1, above, lists peaks at °2θ+0.2°2θ which characterize Form B. The entire list of peaks identified in the XRPD pattern or listed in Table 1, or a subset thereof, may be sufficient to characterize Form B of Compound (I).

3.3° C. and $^{19}$F Solid-State NMR Spectra of Compound (I) Crystalline Form B.

Solid-state NMR spectra were acquired using a Bruker Avance 400 triple-resonance spectrometer operating at a $^1$H frequency of 399.87 MHz. $^{13}$C NMR spectra were obtained using a cross-polarization pulse sequence with a Bruker 4-mm triple resonance magic-angle spinning probe at a rotor frequency of 8 kHz. A linear power ramp from 75 to 90 kHz was used on the $^1$H channel to enhance cross-polarization efficiency. Spinning sidebands were eliminated by a five-pulse total sideband suppression pulse sequence. $^{19}$F spectra were obtained using the same spectrometer and probe, using a cross-polarization pulse sequence and spinning at a rotor frequency of 12.5 kHz. $^{19}$F NMR peak positions are reported relative to CFCl$_3$ and are quoted to a precision of +/−0.2 ppm, because of instrumental variability and calibration. FIG. 3-B shows the solid state $^{13}$C NMR spectrum of Compound (I) crystalline Form B prepared in Example 3.1. The $^{13}$C NMR peak positions are reported relative to tetramethylsilane at 0 ppm (parts per million) and are quoted to a precision of +/−0.2 ppm, because of instrumental variability and calibration. The following peaks were identified in the solid state $^{13}$C NMR spectrum: 171.4, 167.6, 162.7, 160.5, 156.4, 154.3, 151.0, 150.0, 147.4, 139.0, 137.9, 133.5, 131.4, 126.1, 122.7, 117.0, 107.8, 104.3, 100.0, 68.5, 63.9, 56.4, 54.1, 31.9, 29.3, 25.7, and 16.1. Characteristic peaks for Form (B) from the solid state $^{13}$C NMR spectra include those at: 162.7, 160.5, 147.4, 137.9, 133.5, 131.4, 126.1, and 122.7±0.2 ppm. These peaks or a subset thereof may be used to identify crystalline Form B of Compound (I). FIG. 3-C shows the solid state $^{19}$F NMR spectrum of Compound (I) crystalline Form B prepared in Example 3.1. The solid state $^{19}$F NMR spectrum showed peaks −116.1 and −130.4 relative to CFCl$_3$ and with a precision of +/−0.2 ppm, because of instrumental variability and calibration. Both peaks in the solid state $^{19}$F NMR spectra are considered characteristic for Form B. The peaks shown with an asterisk (*) are spinning side bands.

3.4 Raman Spectrum of Compound (I) Crystalline Form B.

Fourier-transform (FT) Raman spectra were acquired using a Thermo Nicolet 960 spectrometer equipped with a liquid nitrogen-cooled germanium detector and a motorized stage accessory with video control. A 1.064 µm laser was used with a power setting of 0.55 W. The powdered sample was placed onto a glass microscope slide and placed directly into the beam using the stage. A 1-mm laser spot size was used, and 512 scans were collected at 2 cm$^{-1}$ resolution. The FT-Raman spectrum of crystalline Form B of Compound (I) is shown in FIG. 3-D. The following peaks (Raman shift, cm$^{-1}$ +/−2 cm$^{-1}$) were observed in the FT Raman spectrum: 391, 460, 636, 705, 750, 787, 853, 911, 1088, 1116, 1163, 1177, 1258, 1305, 1330, 1352, 1386, 1436, 1463, 1483, 1506, 1582, 1623, 1682, 2835, 2967, 3003, and 3076. These peaks or a subset thereof may be used to identify crystalline Form B of Compound (I).

3.3 Thermal Characterization of Compound (I) Crystalline Form B.

DSC thermograms were acquired using a TA Instruments Q2000 Differential Scanning calorimeter. A sample mass of 1.5360 mg of Compound (I) crystalline Form B prepared in Example 3.1 was weighed out directly into an aluminum DSC pan. The pan was sealed by applying pressure by hand and pushing each part the pan together (also known as a loose lid configuration). The temperature was ramped from 25° C. to 225° C. at 10° C./minute. A peak melting temperature of 195.3° C. and a heat flow of 79.18 J/g was measured for the melting endotherm. The DSC thermogram is shown in FIG. 3-E. Exothermic events are plotted in the upward direction.

TGA thermograms were acquired using a TA Instruments Q500 Thermogravimetric Analyzer. The sample pan was tared, and 10.7750 milligrams of Compound (I) crystalline Form B prepared in Example 3.1 was placed in the pan. The temperature was ramped from 25° C. to 300° C. at 10° C./minute. A weight loss of 0.02% was observed up to 150° C., with an additional weight loss of 1.02% up to 180° C., most likely from decomposition. The TGA thermogram is shown in FIG. 3-F.

Example 4

Tablets of Crystalline N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide, Compound (I), Form B Tablets of crystalline Compound 1, Form B, were prepared in four strengths as shown and using the components reported in Table 3. The tablets in this example were prepared with an optional aqueous film coat. The process steps used to form the tablets are set forth in Table 4. Preparation of the intra-granular component involved a high shear wet granulation to make granules to be used for further processing. All components used are conventional for the wet granulation process except for the sodium lauryl sulfate which was added as a bioenhancement agent to enhance the bioavailability of the drug substance. The crystalline Compound (I), form B, was used in a micronized form for bioenhancement, which means that the density of the drug substance is low making it difficult to handle and process. High shear wet granulation is used to produce dense material that is easier to process and make into tablets. The preparation of the extra-granular component was a compression step to make the tablets out of the granules and the added excipients. The excipients used are conventional to allow for the formation of the tablet. The crystalline form of Compound 1, Form B, was retained in the final tablet as confirmed by XRPD.

TABLE 3

| Component | Strength | | | | Function |
| --- | --- | --- | --- | --- | --- |
| | 15 mg | 30 mg | 45 mg | 60 mg | |
| | | mg/tablet | | | |
| Intra-granular Component | | | | | |
| Compound 1, Form B micronized | 15 | 30 | 45 | 60 | Active |
| Lactose Monohydrate | 17.36 | 13.2 | 19.8 | 26.4 | Diluent |
| Microcrystalline Cellulose | 8.75 | 13.2 | 19.8 | 26.4 | Diluent |
| Hypromellose 2910 | 2.19 | 3 | 4.5 | 6 | Binder |
| Sodium Lauryl Sulfate | 0.44 | 0.6 | 0.9 | 1.2 | Wetting Agent |
| Purified Water[1] | | | | | Granulating Fluid |
| Target Granule Weight (mg) | 43.74 | 60 | 90 | 120 | |
| Extra-granular Components | | | | | |
| Microcrystalline Cellulose | 5.19 | 10 | 15 | 20 | Diluent |

TABLE 3-continued

| Component | Strength | | | | Function |
|---|---|---|---|---|---|
| | 15 mg | 30 mg | 45 mg | 60 mg | |
| | | mg/tablet | | | |
| Croscarmellose Sodium | 2.58 | 3.4 | 5.1 | 6.8 | Disintegrant |
| Magnesium Stearate | 0.39 | 0.6 | 0.9 | 1.2 | Lubricant |
| Target Tablet Core Weight (mg) | 51.9 | 74.0 | 111.0 | 148.0 | |
| Aqueous Film Coating (AFC) | | | | | |
| Opadry ® White, YS-1-7706-G[2] | 1.6 | 2.22 | 3.33 | 4.44 | Film Coat |
| Purified water[1] | | | | | Solvent |
| Target AFC Tablet Weight(mg) | 53.5 | 76.22 | 114.33 | 152.44 | |

[1]Purified water is removed during the drying process.
[2]Available from Colorcon, West Point, PA.

TABLE 4

| Step | Ingredients | Process Step |
|---|---|---|
| 1 | Lactose, monohydrate (portion) Micronized GSK1363089G, Microcrystalline Cellulose, Sodium Lauryl Sulfate, Hypromellose, Lactose, monohydrate (remaining portion) (all excipients screened) | → Blending ↓ |
| 2 | Purified Water | → Mixing ↓ |
| 3 | | Drying of Granules (inlet 65 C., exhaust target (50 ± −1 C.); usually 15-30 min) ↓ |
| 4 | | Milling and Screening of Granules ↓ |
| 5 | Microcrystalline Cellulose, Croscarmellose Sodium (all excipients screened) | → Blending ↓ |
| 6 | Magnesium Stearate, screened | → Blending ↓ |
| 7 | | Compression ↓ |
| 8 | Opadry ® White OY-S-28876 Purified Water | → Coating and drying (5-10 min drying, inlet 70-75 C., exhaust typically 50-52 C.) |

The foregoing invention has been described in some detail by way of illustration and example, for purposes of clarity and understanding. The invention has been described with reference to various specific embodiments and techniques. However, it should be understood that many variations and modifications may be made while remaining within the spirit and scope of the invention. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

The claimed invention is:

1. A crystalline form of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide characterized by having at least one of:
   a solid state $^{13}$C NMR spectrum with peaks at 161.2, 158.6, 153.3, 146.5, 136.0, 132.6, 128.6, 127.4, and 124.9 ppm±0.2 ppm;
   a solid state $^{19}$F NMR spectrum with peaks at −116.8 and −128.6 ppm±0.2 ppm relative to $CFCl_3$; and
   an X-ray powder diffraction pattern with peaks at 7.2, 7.7, 12.5, 15.5, 16.5, 17.1, and 19.1°2θ±0.2°2θ.

2. A crystalline form of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide according to claim 1 characterized by at least two of:
   an X-ray powder diffraction pattern with peaks at 7.2, 7.7, 12.5, 15.5, 16.5, 17.1, and 19.1°2θ±0.2°2θ;
   a solid state $^{13}$C NMR spectrum with peaks at 161.2, 158.6, 153.3, 146.5, 136.0, 132.6, 128.6, 127.4, and 124.9 ppm±0.2 ppm; and
   a solid state $^{19}$F NMR spectrum with peaks at −116.8 and −128.6 ppm±0.2 ppm relative to $CFCl_3$.

3. A crystalline form of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide characterized by having at least one of:
   a solid state $^{13}$C NMR spectrum with peaks at 162.7, 160.5, 147.4, 137.9, 133.5, 131.4, 126.1, and 122.7 ppm±0.2 ppm;
   a solid state $^{19}$F NMR spectrum with peaks at −116.1 and −130.4 ppm±0.2 ppm relative to $CFCl_3$; and
   an X-ray powder diffraction pattern with peaks at 6.7, 10.2, 13.1, and 22.2°2θ±0.2°2θ.

4. A crystalline form of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide according to claim 3 characterized by at least two of:
   an X-ray powder diffraction pattern with peaks at 6.7, 10.2, 13.1, and 22.2°2θ±0.2°2θ;
   a solid state $^{13}$C NMR spectrum with peaks at 162.7, 160.5, 147.4, 137.9, 133.5, 131.4, 126.1, and 122.7 ppm±0.2 ppm; and
   a solid state $^{19}$F NMR spectrum with peaks at −116.1 and −130.4 ppm±0.2 ppm relative to $CFCl_3$.

5. Crystalline N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide characterized by having an X-ray powder diffraction pattern with peaks at 11.5, 14.5, 18.3, and 20.4°2θ±0.2°2θ.

6. A pharmaceutical composition comprising a therapeutically effective amount of crystalline N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide according to one of claims 1, 2, 3, 4, or 5 and a pharmaceutically acceptable excipient.

7. A method of treating cancer, comprising the step of administering to a subject in a need thereof a therapeutically effective amount crystalline N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide according to one of claims 1, 2, 3, 4, or 5, wherein the cancer being treated is selected from the group consisting of renal cancer, gastric cancer, head and neck cancer, lung cancer, breast cancer, prostate cancer, colorectal cancer, squamous cell myeloid leukemia, hemangiomas, melanomas, astrocytomas, glioblastomas, hereditary and sporadic renal papilloma, squamous cell carcinoma, hepatocellular carcinoma and brain tumors.

8. A method of preparing crystalline N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide according to claim 1 comprising the steps of:
dissolving N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide in hot n-propanol to form a solution;
cooling the solution sufficiently to afford precipitation of the crystalline form; and
isolating the crystalline form.

9. A method of preparing the crystalline form of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide according to claim 3 comprising the steps of:
adding sufficient heptane to an isopropanol-containing solution of N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide at an elevated temperature to precipitate the crystalline form;
cooling the mixture under conditions sufficient to further precipitate the crystalline form; and
isolating the crystalline form.

10. A method of preparing crystalline N-[3-fluoro-4-({6-(methyloxy)-7-[(3-morpholin-4-ylpropyl)oxy]quinolin-4-yl}oxy)phenyl]-N-(4-fluorophenyl)cyclopropane-1,1-dicarboxamide according to claim 5 comprising the steps of:
dissolving N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide in methanol to form a solution;
allowing the solution to stand under conditions sufficient to precipitate the crystalline form; and
isolating the crystalline form.

* * * * *